United States Patent [19]

Lundsgaard et al.

[11] 4,415,534
[45] Nov. 15, 1983

[54] APPARATUS FOR ANALYZING BIOLOGICAL LIQUIDS

[75] Inventors: Finn C. Lundsgaard, Taastrup; Willy Andersen, Espergaerde, both of Denmark

[73] Assignee: Radiometer A/S, Copenhagen, Denmark

[21] Appl. No.: 308,775

[22] Filed: Oct. 5, 1981

[30] Foreign Application Priority Data

Oct. 6, 1980 [DK] Denmark ............................ 4218/80

[51] Int. Cl.³ .............................................. G01N 1/14
[52] U.S. Cl. ...................................... 422/58; 422/102; 422/104; 422/138; 436/68; 165/32
[58] Field of Search .................. 422/102, 58, 104, 62, 422/138; 165/33, 32; 23/230 B; 436/68

[56] References Cited

U.S. PATENT DOCUMENTS

| | | | | |
|---|---|---|---|---|
| 1,327,207 | 1/1920 | Lidberg | ............................ | 165/33 X |
| 3,246,688 | 4/1966 | Colburn | ............................ | 165/39 |
| 3,763,422 | 10/1973 | MacPhee et al. | ............................ | 23/230 B |
| 4,312,835 | 1/1982 | Zoltan et al. | ............................ | 422/102 |

FOREIGN PATENT DOCUMENTS 464799  4/1937  United Kingdom ............... 165/32

Primary Examiner—Arthur D. Kellogg
Attorney, Agent, or Firm—Hubbell, Cohen, Stiefel & Gross

[57] ABSTRACT

An apparatus for analyzing biological liquids comprises a measuring block including measuring means for measuring characteristics of said liquids. The measuring block is mounted within a thermal shield or housing by means of a base member interconnecting a minor part of the inner wall of the housing and the measuring block so as to define a space between the inner walls of the housing and the measuring block, said space being filled with air or another medium having a poor thermal conductivity.

The thermal shield or housing and the base member are made of a material with good thermal conductivity, and heating and/or cooling means are arranged in heat conductive contact with the said shield. The function of the heating and/or cooling means is controlled by a temperature sensor arranged in heat conductive contact with the measuring block, so as to maintain the temperature of said block at a substantially constant predetermined value.

23 Claims, 2 Drawing Figures

APPARATUS FOR ANALYZING BIOLOGICAL LIQUIDS

BACKGROUND OF THE INVENTION

1. Field of the Invention

The present invention relates to an apparatus for analyzing biological liquids, and especially of the type by means of which it is possible to make very accurate measurements on small liquid samples. In order to obtain the desired accuracy in measurement it is often necessary to secure that the liquid samples which are fed into the apparatus as well as the measuring means of the apparatus are maintained at a substantially constant temperature during measurement.

2. Description of the Prior Art

For the above reason it is usual to arrange the measuring means of the apparatus within a thermally insulated housing and to heat the measuring means to the desired constant temperature by means of a flowing medium, such as air or water, the temperature of which is thermostatically controlled, and the measuring means of the apparatus may possibly be mounted within a block or a measuring body having flow passages formed therein for the liquid samples to be measured, cleaning liquids, salt bridge liquids, etc.

However, the use of such flowing heating mediums involves the use of pumps, blowers, or similar medium circulating means which are undesired because such circulating means increase the complexity of the structure.

U.S. Pat. No. 3,811,493 discloses a thermal shield consisting of a pair of walls defining a space which contains a two-phase heat exchange fluid. The said thermal shield, which is adapted to enclose the upper housing of a gyroscope, is heated by an electric heater, which is arranged at the outer surface of the shield, and controlled by a temperature sensing device mounted on the said upper housing of the gyroscope.

U.S. Pat. No. 3,246,688 discloses an apparatus comprising a centrifuge arranged within an evacuated housing, which may be heated by means of a heating device, the operation of which is controlled by temperature sensors arranged immediately adjacent to the rotating centrifuge and on the said housing, respectively.

It is noted that in the known thermal shields described above a thermostatically controlled heating of the shielding housing itself takes place. If a medium with a temperature differing from that of the shielding housing was continuously or intermittently fed into a device arranged within such a housing, transmission of heat from the shielding housing to the apparatus arranged therein would occur substantially by convection and/or radiation with resulting temperature gradients in the direction from the housing to the apparatus enclosed thereby.

When an apparatus for analyzing biological fluids is in use, liquid samples and possibly also salt bridge liquids, cleaning liquids, and other media are continually fed to the measuring means of the apparatus. Thus, if the temperature control means are adjusted so as to maintain the thermally shielding housing at a temperature above the ambient temperature—as is normally the case—the liquid supplied cause a constant cooling of the measuring means. Therefore, if such a measuring apparatus was arranged in a thermal shield of the type disclosed in the above mentioned U.S. patent a constant transmission of heat from the heated housing to the measuring means arranged therein would take place constantly, and such heat transmission would take place substantially by convection and/or radiation which would give rise to a high thermal time constant between the generator of heat and the temperature sensor.

The prior art also comprises temperature controlled apparatus as those disclosed in U.S. Pat. No. 3,763,422, British Pat. No. 1,488,708, German Auslegeschrift No. 2,039,433, and German Offenlegungsschrift No. 1,523,396.

SUMMARY OF THE INVENTION

The present invention provides an apparatus for analyzing biological liquids, said apparatus having an improved ability to maintain the measuring means of the apparatus and the liquid samples to be measured at a substantially constant temperature.

The invention provides an apparatus for analyzing biological liquids, said apparatus comprising a measuring body including measuring means for measuring characteristics of said liquid, a thermally shielding housing enclosing said body in spaced relationship therewith, said housing being made from a material with good thermal conductivity, and the space defined between said body and said housing containing a medium with poor thermal conductivity, connecting means placing a minor part of said housing in direct heat conductive contact with said body, temperature regulating means arranged in heat conductive contact with said housing, and a temperature sensor arranged in heat conductive contact with said body for controlling the function of said heat regulating means so as to maintain the temperature of said body at a substantially constant predetermined value.

Because the measuring body which includes the measuring means is in direct heat conductive contact with the thermally shielding housing, the temperature regulating means, which may be heating and/or cooling means, may simultaneously heat or cool the housing and the measuring body as well as the heating means arranged therein or thereon by heat conduction. This means that no substantial heat gradients occur between the housing and the measuring body and, therefore, a very accurate control of the temperature of the measuring body and of the associated measuring means as well as of the liquid within said measuring body may be obtained. As the transmission of heat between the housing and the measuring body takes place by conduction in a material having good heat conducting characteristics, the desired temperature is obtained more quickly in the apparatus according to the invention than in the above mentioned known apparatuses in which the heat transmission is based on convection. Furthermore, due to the good heat conductivity of the thermally shielding housing compared to the heat conductivity of the medium within the space defined between said body and said housing, a possible local heating or cooling of the shielding housing will not give rise to a corresponding local temperature change of the measuring body. The ratio between the specific heat conductivity of the medium within the said space and of the thermally shielding housing is preferably less than $10^{-3}$, and suitable materials by means of which such conductivity ratios may be obtained include gas or atmospheric air, foamed plastic, or granular plastic in air as far as the medium in the said space is concerned, and aluminum as far as the housing is concerned.

The temperature regulating means may be arranged on the thermally shielding housing in a known manner. However, in principle the said temperature regulating means may be arranged on the measuring body which is in direct heat conductive connection with the housing. Furthermore, temperature regulating means in the form of heating and/or cooling means may be arranged on the housing as well as on the measuring body. However, it is preferred to arrange the temperature regulating means immediately adjacent to the location at which the measuring body is connected to the housing, whereby the housing as well as the measuring body may quickly be heated and/or cooled by the same means. It is also possible to provide one or more further thermally shielding and mutually spaced housings enclosing the housing which is connected to the measuring body.

If desired, two or more temperature sensors may be used. One of these sensors may then be arranged in contact with the measuring body, while the other may be arranged on the thermally shielding housing. If only one temperature sensor is used it may be arranged adjacent to the measuring body, for example adjacent to the location at which the measuring body is connected to the housing. However, the temperature sensor is preferably arranged on or within the measuring body proper or adjacent to the measuring means or adjacent to the location at which the measuring body is connected to the housing.

In order to obtain an improved thermostatic temperature control of the measuring body it is important that the liquid, for example in the form of liquid samples, salt bridge liquid, and/or cleaning liquid, which is introduced into the measuring body, obtains a temperature, which substantially corresponds to the thermostatically set temperature, before introduction of the liquid. Therefore, a substantial length of a conduit for feeding liquid to the measuring means in the measuring body may extend in heat conductive contact with the thermally shielding housing. Thereby, the cooling of the measuring body caused by the introduction of the liquid is reduced. The said heat conductive contact between the thermally shielding housing and the liquid feeding conduit or conduits may be obtained in any other suitable manner. As an example, part of at least one of the liquid feeding conduits may extend in a channel or groove formed at the wall or walls of the said housing. These channels or grooves may be formed so as to extend along the inner surface of the wall or walls of the housing, or they may extend transversely to the said wall or walls.

In a preferred embodiment of the apparatus according to the invention the measuring body is mounted on a heat conducting base member arranged on the inner surface of the housing. The measuring body may then be arranged suitably spaced from the walls of the housing and nevertheless be in good heat conductive contact with the housing via the base member. In this embodiment part of the liquid feeding conduit or conduits may advantageously extend within or in direct contact with the said base member, whereby the desired preheating of the liquid may be obtained.

In order to reduce the risk that a possible local temperature influence of the thermally shielded housing and the consequent temperature gradient in the housing are transmitted to the measuring body through the base member, this base member is preferably shaped so as to have a relatively small minimum cross-sectional area forming a kind of a "strait gate" in the heat conducting connecting formed by the base member between the measuring body and the housing. Thus, the base member may, for example, have a relatively small uniform cross-sectional area along the total length thereof, or the base member may be tapered in the direction of one of its ends or both of its ends, or the base member may have an hourglass-like shape. Generally speaking, the minimum cross-sectional area of the base member should preferably be substantially smaller than the maximum cross-sectional area or extension of the measuring body.

The temperature regulating means may comprise heating means, for example in the form of a power transistor. In cases where the ambient temperatures exceed or are close to the desired thermostatically set temperature the said heating means may be replaced by or supplemented by cooling means, for example in the form of a Peltier cell. The temperature sensor which controls the operation of the heating and/or cooling means may, for example, be a thermistor.

BRIEF DESCRIPTION OF THE DRAWING

The invention will now be further described with reference to the drawing, wherein.

DESCRIPTION OF THE PREFERRED EMBODIMENT

Figure 1:
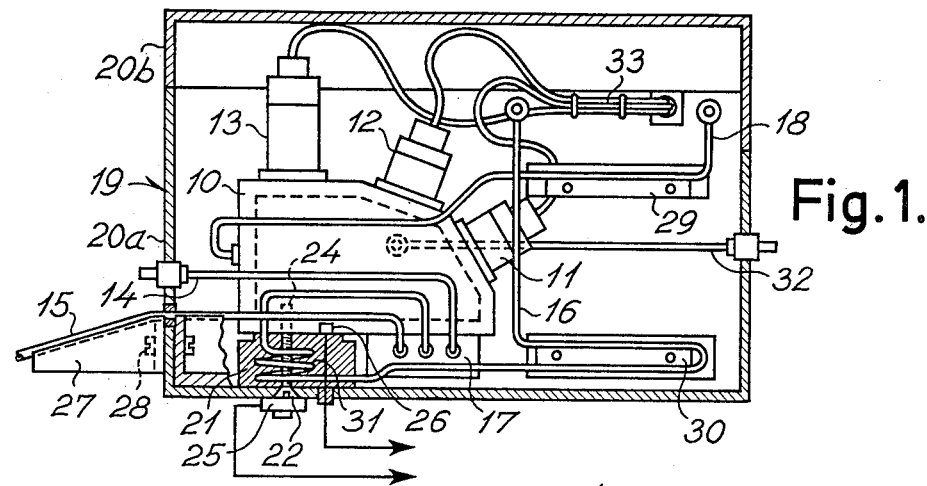
FIG. 1 is a sectional view of an embodiment of the apparatus according to the invention.
Figure 2:
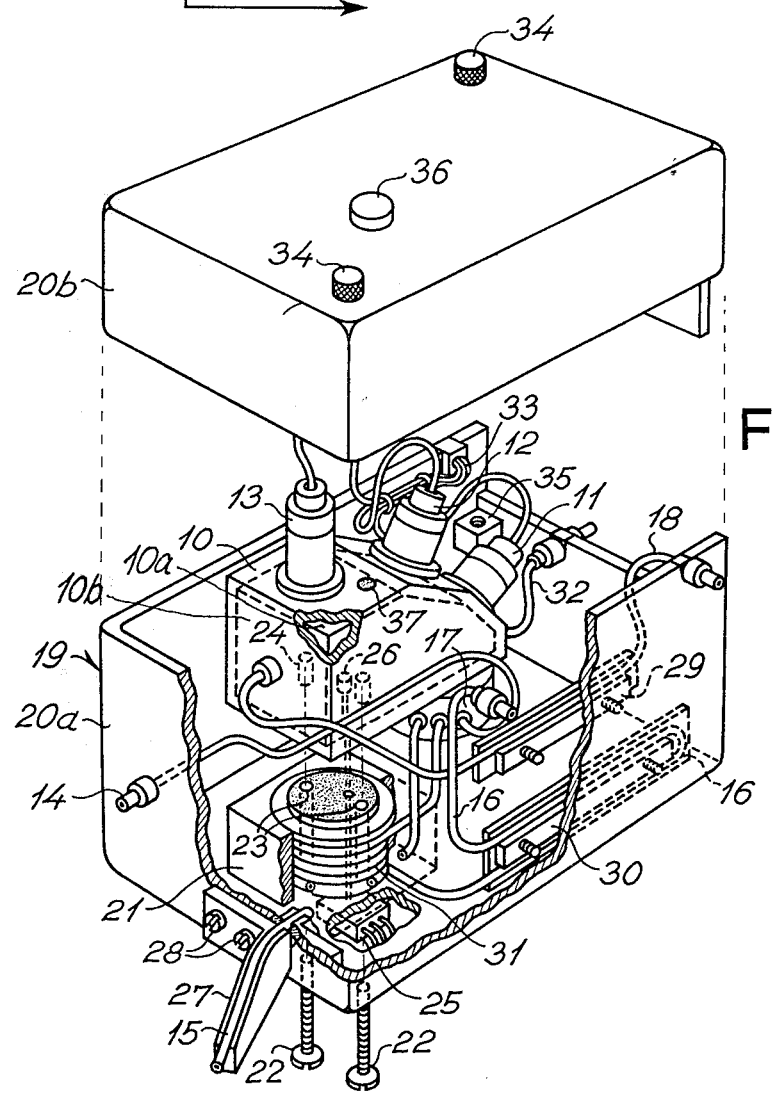
FIG. 2 is a perspective view of the apparatus shown in FIG. 1, the parts of the housing being shown in a separated condition, and parts of the apparatus having been cut away.

The apparatus shown in the drawing is a blood analyzing apparatus comprising a measuring body or a measuring block 10 which may be made from metal. However, as indicated in FIG. 2 the measuring block preferably includes a body 10a made of glass ceramics and containing various measuring chambers and connecting passages, and a jacket 10b which is made of metal, for example aluminum, and which closely surrounds the body 10a. The body 10a of glass ceramics is preferably of the type disclosed in U.S. Pat. No. 4,160,714. Three plane surfaces defining obtuse angles therebetween are formed at the upper side of the measuring block, and an electrochemical electrode is mounted on each of these plane surfaces, namely a calcium electrode 11, a pH-electrode 12, and a reference electrode 13, respectively. The apparatus may operate in a manner known per se, so that blood samples to be analyzed is automatically introduced through a sample feeding tube 14. However, the apparatus may also be set for semi-automatic function, and the blood samples to be analyzed are then fed into the apparatus through a sample feeding tube 15. These sample feeding tubes 14 and 15 and a feeding tube 16 for cleaning or rinsing liquid lead to an automatically controlled valve mechanism 17 arranged on the bottom surface of the measuring block 10. During the measuring cycle of the apparatus the valve mechanism 17 automatically controls the feeding of blood samples into the measuring chambers associated with the measuring electrodes 11 and 12, and the feeding of rinsing or flushing liquid into the measuring chambers after termination of each measurement of a blood sample and before the next measurement takes place. A salt bridge liquid, such as KCl, is fed to the reference electrode 13 through a feeding tube 18.

The measuring block 10 is mounted within and completely surrounded by a housing 19 comprising a container part 20a and an associated cover part 20b. The housing 19 is made from metal, such as aluminum, or from another material with a good heat conductivity. The measuring block 10 is mounted on a base member 21 extending between the bottom side of the block 10 and the bottom wall of the housing 19. The base member 21 is also made of metal, preferably aluminum, or of another material with good heat conductivity. The measuring block 10, the base member 21, and the housing 19 may be clamped together by means of a pair of screws 22, which extend through through-going bores 23 in the base member 21, and which are screwed into threaded bores 24 formed in the bottom side of the measuring block 10. In order to obtain a good heat conductive connection between the housing 19 and the measuring block 10 the contacting surfaces between the base member 21 and the bottom wall of the housing 19 and the bottom side of the measuring block 10, respectively, are preferably provided with heat conducting silicone fat or a similar paste-like heat conducting material. A power transistor 25 is arranged on the bottom side of the housing 19 immediately below the base member 21, and a temperature sensor 26, which may be in the form of a thermistor, is arranged between the upper contact surface of the base member 21 and the measuring block 10 in a recess formed in the bottom surface of the latter. The power transistor 25 and the thermistor 26 are included in a temperature control circuit which, in a manner known per se, controls the power supply to the transistor 25 so as to maintain the temperature of the measuring block 10 and consequently of the electrodes 11 to 13 and of the liquids supplied thereto at a substantially constant, set temperature. Because the base member 21 secures a good heat conducting connection between the measuring block 10 and the housing 19 which is also made of a good heat conducting material, the temperature control means described secure that the housing 19 is kept at substantially the same temperature as the measuring block 10 so that no substantial temperature gradients occur within the air filled space defined between the outer surface of the measuring block 10 and the inner surface of the housing 19.

In order to reduce temperature gradients within the measuring block 10 it is tried to adjust the temperature of the liquids introduced into the measuring block to substantially the same temperature as that of the measuring block, before the said liquids are introduced into the measuring block. This may, for example, be obtained by placing a length of one or more of the liquid feeding tubes in heat conductive contact with the housing 19. Thus, a length of the sample feeding tube 15 for semi-automatic introduction of samples is arranged within a spout-like channel 27, which extends outwardly from the end wall of the housing, and which is fastened to the outer surface of said end wall of the housing by means of screws 28. Similarly, parts of the feeding tubes 16 and 18 for rinsing liquid and salt bridge liquid, respectively, are arranged in channels defined between the inner surface of a side wall of the housing 19 and metal strips or rails 29 and 30, respectively, which are fastened to the inner surface of the said side wall, for example by screws. Additionally, a substantial length 31 of the feed tube 16 for rinsing liquid is helically coiled and arranged within the base member 21 and in heat conductive contact therewith.

The liquid supplied to the measuring block 10 through the feed tubes described above may be discharged from the measuring block through a common liquid discharge tube 32, and the electrodes 11 to 13 are connected to the electronic circuit (not shown) of the apparatus by means of conductors or cables 33. As shown in FIG. 2, the cover portion 20b of the housing 19 is removably fastened to the container part 20a by means of finger screws 34 which may be screwed into corresponding threaded bores formed in blocks 35 which are arranged at two diagonally opposite corners of the housing. Furthermore, the cover portion 20b is provided with a removable stopper 36, and when the stopper has been removed a thermometer may be passed through the cover part and inserted in a pocket or bore 37, which is formed in the upper side of the block 10, and which may contain silicone fat or another suitable medium.

As the apparatus operates in a known manner as far as the measuring function is concerned, and as this measuring function is of no importance for the present invention, this measuring function will not be described more in detail. However, in the apparatus shown and described a good and simple thermostatic temperature control of the measuring block 10 may be obtained because heat is supplied to the block from the power transistor 25 through the base member controlled by the temperature sensor 26 which is in contact with the block, while the measuring block is also surrounded by the housing 19, which are maintained at substantially the same temperature as the measuring block 10 by the same temperature control means, whereby the housing serves as a thermal shield for the measuring block.

It has been found that in a practical embodiment of the apparatus according to the invention it is possible to obtain a temperature control with an accuracy of 37° C.±0.1° C. at ambient temperatures varying between 15° and 32° C.

While a preferred embodiment has been described above with reference to the drawing, it should be understood that various changes and modifications of this embodiment may be made within the scope of the present invention. Thus, the measuring block may be surrounded by two or more thermal shields or housings which may possibly be temperature controlled independently. Furthermore, the device 25 may be a thermostatically controlled cooling device, for example in the form of a Peltier cell. This especially advantageous when it may be expected that the ambient temperature will exceed or be about the desired temperature of the measuring block 10.

We claim:

1. An apparatus for analyzing biological liquids, said apparatus comprising
   a measuring body including measuring means for measuring characteristics of said liquid,
   a thermally shielding housing enclosing said body in spaced relationship therewith, said housing being made from a material with good thermal conductivity, and the space defined between said body and said housing containing a medium with poor thermal conductivity,
   heat conductive connecting means placing a minor part of said housing in direct heat conductive contact with said body,
   temperature regulating means arranged in heat conductive contact with said housing, and a temperature sensor arranged in heat conductive contact with said body for controlling the function of said heat regulating means so as to maintain the temperature of said body at a substantially constant predetermined value.

2. An apparatus according to claim 1, wherein said measuring body is in the form of a block.

3. An apparatus according to claim 2, wherein said measuring means extend into bores or depressions formed in said block.

4. An apparatus according to claim 1, wherein said temperature regulating means are arranged adjacent to the location at which said body is in heat conductive contact with said housing.

5. An apparatus according to claim 1, wherein the temperature sensor is arranged on the measuring body adjacent to the location where said body is in direct heat conductive contact with said housing.

6. An apparatus according to claim 2, further comprising at least one conduit for feeding liquid to said measuring means in said block, a substantial length of said feeding conduit extending in heat conductive contact with said housing.

7. An apparatus according to claim 6, wherein said feeding conduit extends in a channel or groove formed at the wall of said housing.

8. An apparatus according to claim 2, wherein said connecting means comprise a heat conductive base member having its one end part mounted on the inner wall of said housing, the measuring body being mounted on the other end portion of the base member.

9. An apparatus according to claim 8, wherein the minimum cross sectional area of said base member is substantially smaller than the maximum cross sectional area of the said block.

10. An apparatus according to claim 8, further comprising conduits for feeding liquid to said measuring means, at least one of said feed conduits extending within said base member.

11. An apparatus according to claim 3, wherein said measuring body comprises a block-shaped body of glass ceramics in which said bores or depressions are formed, the outer surface of said block being covered by a layer of metal.

12. An apparatus according to claim 11, wherein said metal is aluminum.

13. An apparatus according to claim 1, wherein said temperature regulating means comprise a power transistor.

14. An apparatus according to claim 1, wherein said temperature regulating means comprise a Peltier cell.

15. An apparatus for analyzing biological liquids, said apparatus comprising
a measuring block including measuring means arranged in bores or depressions formed in said block,
a thermal shield enclosing said block in spaced relationship therewith, said shield being made from a material with good thermal conductivity, and the space defined between said block and said shield containing a medium with poor thermal conductivity,
a base member with good thermal conductivity interconnecting a minor inner wall part of said shield and said block so as to establish direct heat conductive contact between said shield and said block,
temperature regulating means arranged in heat conductive contact with said shield, and
a temperature sensor arranged in heat conductive contact with said block for controlling the function of said heat regulating means so as to maintain the temperature of said block at a substantially constant predetermined value.

16. An apparatus according to claim 15, wherein said temperature regulating means are arranged on said shield adjacent to said base member.

17. An apparatus according to claim 15, wherein said temperature sensor is arranged on said measuring block adjacent to said base member.

18. An apparatus according to claim 15, further comprising at least one conduit for feeding liquid to said measuring means in said block, a substantial length of said feeding conduit extending in heat conductive contact with said shield.

19. An apparatus according to claim 18, wherein said feeding conduit extends in a channel or groove formed at the wall of said shield.

20. An apparatus according to claim 15, wherein the minimum cross-sectional area of said base member is substantially smaller than the maximum cross sectional area of the said block.

21. An apparatus according to claim 15, further comprising conduits for feeding liquid to said measuring means, at least one of said feeding conduits extending within said base member.

22. An apparatus according to claim 15, wherein said temperature regulating means comprise a power transistor.

23. An apparatus according to claim 15, wherein said temperature regulating means comprise a Peltier cell.

* * * * *